June 19, 1973 H. KERRIGAN Plant Pat. 3,363
AZALEA PLANT
Filed Oct. 18, 1971
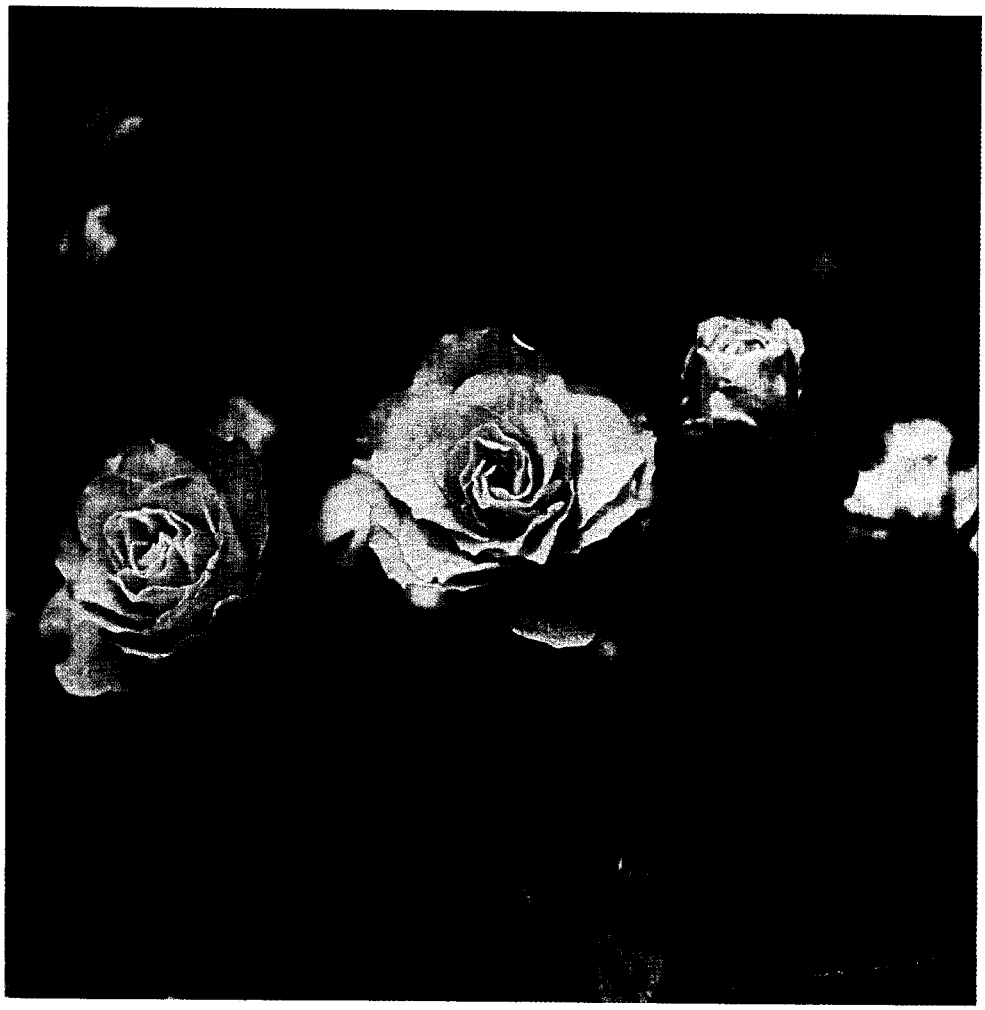

United States Patent Office

Plant Pat. 3,363
Patented June 19, 1973

3,363

AZALEA PLANT

Howard Kerrigan, 25783 Mission Blvd., Hayward, Calif.

Filed Oct. 18, 1971, Ser. No. 190,237
Int. Cl. A01h *5/00*
U.S. Cl. Plt.—56 1 Claim

The invention relates to a new and distinct variety of azalea plant of the Belgian-Indica type, originated by me in 1953 as a consequence of a breeding program begun in 1943. The parentage of my new azalea plant is as follows: Jean Hearren (unpatented) the seed parent×Lorna (unpatented) the pollen parent.

The object of the cross was to produce a late flowering double florist azalea more double and much later flowering form than exists at present in the trade. These objectives were achieved along with other desirable improvements, as evidenced by the following unique combination of characteristics which are outstanding in the new variety and which distinguish it from its parents as well as from all other varieties of which I am aware. My new variety is primarily characterized by: a combination of full, double, salmon pink blooms borne in profusion on a vigorous, but well branched plant which blooms much later than any double varieties now in the florist trade.

Asexual reproduction of my new variety by cuttings, through a series of annual propagations at Oakland and Hayward, Calif. in 1957 shows that all characteristics of the variety come true to form through succeeding propagations. The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of one, two, three year old flowering plants at Hayward, Oakland, and Santa Rosa, Calif.

The plant is low growing spreading, dense, compact heavily branched to 24″ tall by 30–36 inches across. The branches are densely strigose, the strigae completely covering the young stems. The strigae are coarse, broad based, pointed, about five to six times as long as broad, tip hyaline to translucent, bases opaque and dull brown. Very young growth is pale green with subhyaline tan strigae. The strigae darken with age. The foliage is ordinary except that the tomentum above is finer than that below.

The flowers are fully double China Rose (HCC 024/2). The peduncle is short, stout, pubescent, ¼–⅜″ long by 3/32″ broad. The tomentum consists of tan strigae especially at the base and dense hyaline short pubescence. The calyx is abruptly truncate at the base, petalaceous with greenish overlays. The flaring portions of the lobes are variable in shape and size, all different and some with medial sinuses. The dorsal portion of the calyx tube is spotted green and green patches occur at the base of the medial sinuses. The corolla is truncated at the base of the tube but less so than the calyx. Greenish and red spotting occurs on the dorsal lobes. The staminodia are free or fused in pairs, triplets and an occasional quadruplet. The staminodia are reduced centripetally, becoming colorless and rudimentary in the center. Typical flowers contain 35–45 single staminodia. 7–12 double, 2–5 triple and 1–2 quadruple arranged completely randomly. An average of about 50–60 staminodia occur, derived from about 80–85 stamens. The pistil is rudimentary or Having thus disclosed my invention, I claim:

1. A new and distinct variety of azalea plant, of the Belgian-Indica type substantially as herein shown and described primarily characterized by: a combination of full, double, salmon pink blooms borne in profusion on a vigorous, but well branched plant which blooms much later than any double varieties now in the florist trade.

No references cited.

ROBERT E. BAGWILL, Primary Examiner